(12) United States Patent
Faure et al.

(10) Patent No.: US 8,709,796 B2
(45) Date of Patent: Apr. 29, 2014

(54) DEVICE FOR PREPARING A BODY FLUID FOR A BACTERIOLOGICAL ANALYSIS

(75) Inventors: Isabelle Besson Faure, Yerres (FR); Jean-Pierre Hermet, Boulogne (FR); Sébastien Ribault, Romanswiller (FR)

(73) Assignee: Becton, Dickinson and Company, Franklin Lakes, NJ (US)

(*) Notice: Subject to any disclaimer, the term of this patent is extended or adjusted under 35 U.S.C. 154(b) by 1697 days.

(21) Appl. No.: 11/995,355

(22) PCT Filed: Jul. 11, 2006

(86) PCT No.: PCT/FR2006/001690
§ 371 (c)(1),
(2), (4) Date: Apr. 28, 2008

(87) PCT Pub. No.: WO2007/006972
PCT Pub. Date: Jan. 18, 2007

(65) Prior Publication Data
US 2008/0213819 A1  Sep. 4, 2008

(30) Foreign Application Priority Data
Jul. 12, 2005 (FR) ...................................... 05 52151

(51) Int. Cl.
*C12M 1/00* (2006.01)
*C12M 3/00* (2006.01)
*C12M 1/14* (2006.01)
*C12M 3/04* (2006.01)
*B01D 35/00* (2006.01)
*B01D 35/14* (2006.01)
*B01D 17/00* (2006.01)
*C02F 9/00* (2006.01)

(52) U.S. Cl.
USPC .................. 435/299.1; 435/298.1; 435/297.5; 435/283.1; 435/289.1; 210/85; 210/86; 210/87; 210/188; 210/252

(58) Field of Classification Search
USPC .......... 435/298.1, 297.5, 299.1, 283.1, 289.1; 210/85, 86, 87, 188, 252, 739, 806; 600/583, 584
See application file for complete search history.

(56) References Cited

U.S. PATENT DOCUMENTS 5,858,253 A * 1/1999 Holm ............................ 210/702
6,755,802 B2 * 6/2004 Bell ............................ 604/6.15
(Continued)

FOREIGN PATENT DOCUMENTS

EP  0 122 581  10/1984
FR  2 853 326  10/2004
(Continued)

OTHER PUBLICATIONS

International Search Report dated Nov. 23, 2006 for Application No. PCT/FR2006/001690, filed Jul. 11, 2006.
International Preliminary Report on Patentability and Written Opinion dated Jan. 16, 2008 for Application No. PCT/FR2006/001690, filed Jul. 11, 2006.

*Primary Examiner* — Nathan Bowers
*Assistant Examiner* — Lydia Edwards
(74) *Attorney, Agent, or Firm* — Knobbe, Martens, Olson & Bear LLP

(57) ABSTRACT

The invention concerns a device for preparing a body fluid for a bacteriological analysis thereof comprising a container provided with a chamber (4) wherein a piston (5) is mobile between an opening position and a closing position, the chamber (4) including a separation zone (7) and means for introducing (15, 16) a fluid into said chamber and the piston (5) including a closure means (8) co-operating with the separation zone (7) so as to define an upper volume (9) and a lower volume (10) on either side of said zone, the upper volume (9) and the lower volume (10) mutually communicating when the piston (5) is in opening position and being tightly isolated from each other when the piston (5) is in closing position. The invention also concerns a preparation method using such a device (1).

19 Claims, 1 Drawing Sheet

(56) References Cited

U.S. PATENT DOCUMENTS

| | | |
|---|---|---|
| 6,869,769 B2 | 3/2005 | Burgoyne |
| 2004/0170535 A1* | 9/2004 | Noda .......................... 422/101 |
| 2004/0208796 A1 | 10/2004 | Chiga |

FOREIGN PATENT DOCUMENTS

| | | |
|---|---|---|
| WO | WO 95/02050 | 1/1995 |
| WO | WO 95/04098 | 2/1995 |
| WO | WO 01/32828 A2 | 5/2001 |

\* cited by examiner

DEVICE FOR PREPARING A BODY FLUID FOR A BACTERIOLOGICAL ANALYSIS

The present invention refers to the field for preparation of samples of biological fluid, more specifically blood, for their biological analysis.

The present invention refers more specifically to the field of microbiology and proposes a method and a device for sampling and treating a volume of whole blood for bacteriological analysis.

The method and device described in the present invention are designed for removing a sample of whole blood, for reducing/removing the eukaryotic/human cells present in this sample and for isolating/concentrating the prokaryotic/microorganismal cells possibly present in this sample for their detection and/or identification by specific methods. Among these methods, the following may be mentioned: ① cell biology methods such as culture in Petri dishes, direct detection techniques with the microscope and ② molecular biology methods of DNA and RNA analysis, for example with the RFLP (restriction fragment length polymorphism) method and the DNA amplification method or PCR (polymerase chain reaction) with the real time PCR method in particular.

Blood is normally sterile. It is necessary to be able to demonstrate possible bacteremia, delay in management of the patient and therefore delay in diagnosis playing a part in the frequency of deaths. Therefore, the method enabling detection and identification of bacteria present in blood is necessary. At the present time, standard microbiological techniques are used which consist successively of hemoculture, first visual identification after Gram staining and then subculture on solid medium for secondary identification and antibiogram. Results are generally obtained within several days. The other molecular biology type of methods used only enable precise identifications that are linked to particular indications, for example, detection of group B *streptococcus* during pregnancy.

The results of biological tests carried out on blood samples are very dependent on preanalytical conditions. In fact, the type of sample made (venous or arterial), the anticoagulant used, the material available significantly influence the quality of the results. In addition, for bacteriological analysis, the test conditions should resort to strict procedures in order to avoid any contamination during handling, leading to results known as "false positives" from microorganisms present in the environment. These conditions have to be even more drastic for molecular biology analyses which resort to reagents that are highly sensitive to interferences naturally present in the environment. The variability in preanalytical conditions combined with the multiplicity of detection/identification methods make the bacteriological blood test with molecular biology a parameter that is standardizable with difficulty. In fact, the preparation of samples for bacteriological analysis usually resorts to "house" unstandardized techniques to be carried out in a sterile environment with material specific for this application. The device described in the present invention is a standardization path. It is a closed system without risk of contamination of the sample. Sampling is done directly in the sample tube by aspiration without opening the latter and all the preparation steps are carried out within the device without breaking the sterility.

In the laboratory, PCR generally enables detection by amplification of several copies of the bacterial genome in a sample. It is a rapid analysis that is carried out in several hours and that also makes it possible to learn the species of bacteria in question. However, the use of molecular biology methods is limited in part by the presence of numerous factors in the blood which reduce the efficacy of the amplification, such as the immunoglobulins G with a plasma concentration of 8-18 g/liter, heme, hemoglobin, the main component of red blood cells and lactoferrin, present in leukocytes, high concentrations of eukaryotic DNA coming from nucleated blood cells such as leukocytes. Because of this, the volumes analyzed are low to limit the quantity of inhibitors: with the methods currently available on the market, the treatable volume of sample is 100 µL, and it rarely exceeds 200 µL, according to the kits. In the case of symptomatic bacteremias or asymptomatic bacteremias, the bacterial load is very low and may be less than 1 bacterium per milliliter of blood. In this case, it is statistically demonstrated that 200 µL is an insufficient volume to detect low concentrations. The device described in the present invention enables the plasma and cell inhibitors to be reduced, making it possible to expand the volume up to 15 mL of whole blood and because of this, an increase in the sensitivity of the method.

In order to be free of the cellular inhibition factors, the PCR methods are usually carried out on serum derived from centrifugation of whole blood. In fact, during centrifugation, the cells in the blood are concentrated in the pellet while the soluble compounds such as free DNA and RNA remain in the supernatant which is sampled for analysis. This method does not apply to bacteria because their density is comparable to that of the cells in the blood and they are also found in the cell pellet.

In the U.S. Pat. No. 6,869,769, a device, a method and a kit are described to separate the cells in the blood (leukocytes, red blood cells, platelets) from viral DNA/RNA or bacterial DNA on a solid support for PCR analysis. This method can only be applied on volumes of blood that are extremely reduced on the order of a drop and cannot be applied to research and/or identification of microorganisms in the case of bacteremia where the load of microorganisms is very low.

The invention aims to improve the drawbacks and the shortcomings in the state of the art by proposing a device and a method facilitating the rapid sample analysis of biological fluid in the field of microbiology effectively, in a standardized way and simply with a reduced exposure of the user with respect to biological risks. This method and this device are particularly adapted to a routine use in the hospital sector for preparation of a blood sample for bacteriological analysis, in particular by molecular biology, that enables the biologist and the clinician to rapidly access a result.

For this purpose and according to a first aspect, the invention concerns a device for preparation of a sample of biological fluid for its bacteriological analysis and comprising a container provided with a chamber in which a piston is movable between an open position and closing position, the chamber comprising a separation zone and a means for introduction of a fluid into said chamber, said means of introduction being arranged in the upper part of the chamber and the piston comprising a closure means working together with the separation zone in order to define an upper volume and a lower volume on both sides of said zone, the upper volume and the lower volume communicating with each other when the piston is in the open position and tightly isolated from each other when the piston is in the closing position.

The device described in the present invention is the connection between the sample of blood to be tested and the analysis platform; it is part of the overall and standardized solution for rapid detection of bacteria in the blood. The device consists of different independent but connected volumes that may contain solutions of ready-to-use reagents.

During its use in the hospital, the device enables different sequential and integrated steps to be carried out.

According to a second aspect, the invention concerns a method for preparation of a sample of biological fluid for its bacteriological analysis using a device for preparation as described above, said method comprising steps consisting of:

introducing the biological fluid into the chamber, the piston being in the open position;

after sedimentation of the biological fluid, moving the piston in its closing position in order to separate the sediment pellet from the supernatant, said pellet being found in the lower volume and said supernatant being found in the upper volume;

mixing the supernatant with a solution of reagents put together to promote the growth of microorganisms present in said supernatant;

sampling said supernatant for its bacteriological analysis.

More specifically, the device enables sampling or receiving in a sterile way a sample of 1 mL minimum to 15 mL maximum of whole blood derived from a standard blood sampling tube sampled on anticoagulant.

The device associated with the sampling tube enables the sample to be taken by an aspiration system (bellows, bulb, piston).

The device enables incubation in the chamber for a period from 20 min to 60 h, a time during which the red blood cells sediment in the pellet and the microorganisms grow. This chamber may be filled with a first solution of reagents accelerating the sedimentation of the red blood cells and/or the growth of the microorganisms.

The device enables 6-20 mL of supernatant resulting from the previous step to be sampled or isolated without sampling the pellet present in the lower volume.

The device enables the mixture of this supernatant with a second solution of reagents in the chamber or after transfer to a second chamber. The whole unit is incubated with shaking for 30 min to 6 h, the period during which the platelets aggregate and the microorganisms grow.

The device enables the filtration of the entire resulting sample on a syringe filter with porosity greater than 5 µm with a "luer" connector (female "luer lock" inlet, male "luer" or "luer lock" outlet) to retain the platelet aggregates/clumps and the residual white blood cells and, in line, a membrane support for the female "luer lock" inlet connector formed of two overlapped and detachable parts containing a 0.2-1 µm porosity membrane filter retaining the bacteria. An example of the membrane support is described in the patent US-2004/0208796.

The bacteria isolated on this latter membrane may then undergo preparation for molecular biology analysis. Usually, physical or chemical or physicochemical lysis is applied to break the cells and recover the genetic material to be analyzed. The advantage of pretreatment of the sample by means of the method and device described in this invention is to differentiate the microorganisms of interest from all the factors that interfere in the tests, plasma-soluble factors or cellular factors. To do that, the different chambers of the device may contain solutions of ready-to-use reagents:

The first solution in the chamber is composed of reagents that accelerate the sedimentation of the red blood cells and the growth of the microorganisms:

Culture medium for microorganisms;
Polymers;
Agglutinins;
Osmosed water.

The second solution in another chamber (or added to the chamber of the device) is composed of reagents that enable the aggregation of platelets and growth of the bacteria:

Culture medium for microorganisms;
Platelet aggregation agent.

Other objects and advantages of the invention will appear during the description that follows, made in reference to the attached drawings.

Figure 1:
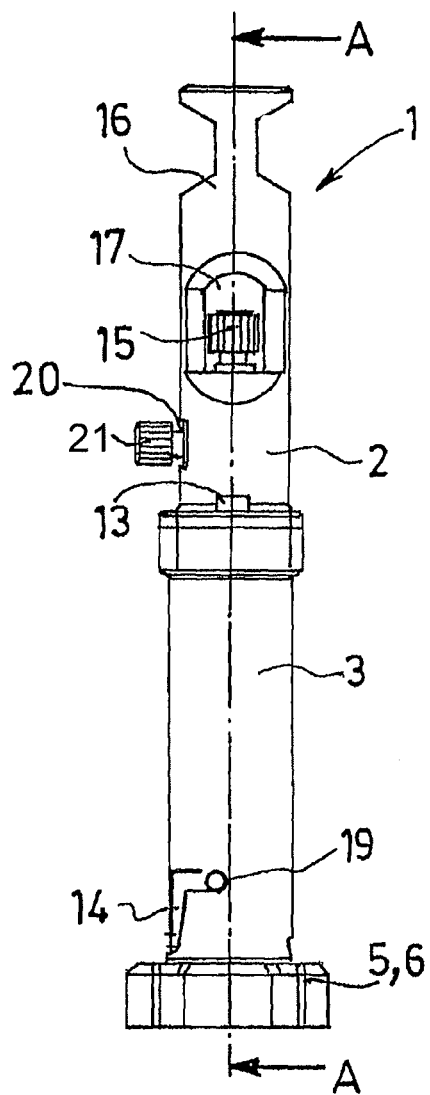
FIG. 1 is a diagrammatic representation of the side of the device according to the invention.
Figure 2:
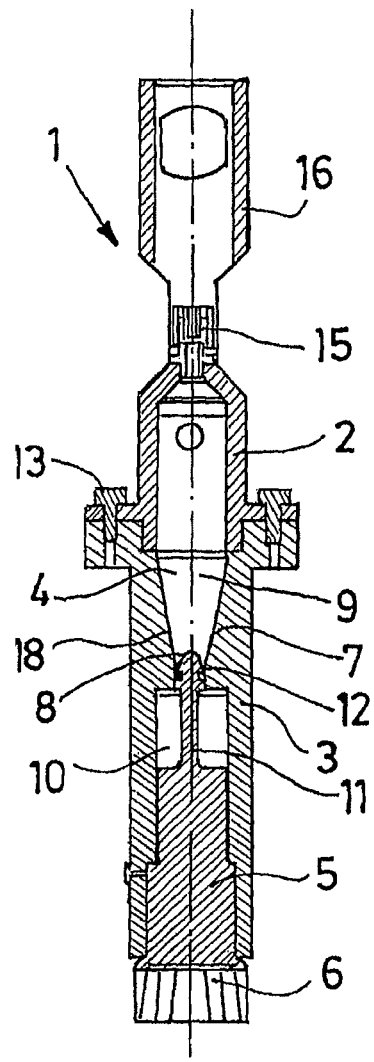
FIG. 2 is a cross-sectional diagrammatic representation along axis A-A of FIG. 1.

In reference to the figures, device 1 is described for preparation of a sample of biological fluid, including three principal assembled parts defining a container. The upper part 2 of the device is associated with the lower part 3 to form a chamber 4 closed at its base by a piston 5 that is movable between an open position and a closed position in the lower part 3 of the device and that also forms the base 6 of the device. The chamber 4 consists of a separation zone 7. The piston 5 consists of a closure means 8 cooperating with the separation zone 7 in order to define an upper volume 9 and a lower volume 10 on both sides of zone 7. The upper volume 9 and the lower volume 10 communicate with each other when piston 5 is in the open position and are tightly isolated from each other when piston 5 is in the closed position, as represented in FIG. 2.

Piston 5 consists of a rod 11 that extends into the lower volume 10, said lower volume extending on both sides of the rod 11. Rod 11 consists of a protuberance 12 forming a closure means 8 provided in its extreme free part.

The upper 2 and lower 3 parts are assembled by means of screw 13 or may be glued. The lower part 3 consists of a guiding groove 14 and the piston 5 consists of a pin 19, said pin being arranged in said groove. Piston 5 is found in the closing position when the pin 19 is arranged on one of the extreme parts of the groove 14, as represented in the figures and in the open position when pin 19 is arranged in the other extreme part of the groove 14.

Advantageously, the device is made of siliconized glass or plastic material to which cells do not adhere, for example, polypropylene or polyacrylic of the polymethyl methacrylate type. The material of the device should be compatible with sterilization, preferably by β or γ irradiation. The protuberance 12 of the closure means 8 is preferentially an elastomer to ensure tight closing that is adapted to the diameter of the device.

The different steps of the method in relation to the structure of the device are detailed below. During the first step, the sample is introduced by the upper part 2 of the device by means of introduction of the fluid into the chamber 4. The means of introduction are for example, formed by a Luer connector 15. A pump body equipped with a protected needle capable of piercing the rubber stoppers of the sampling tubes is screwed on the Luer connector 15 on the upper part of the device. The pump body is kept in a receiving part 16 associated with the upper part of the container. The receiving part is formed for example, by a skirt with a diameter greater than the diameter of the pump body receiving the tube. The skirt is pierced by two windows 17 that allow handling (screwing-unscrewing) of objects placed on the Luer 15. The sampling tube containing the blood is positioned stopper to bottom and is guided on the needle in the body of the pump. By exerting vertical pressure on the tube, the rubber stopper is pierced and the needle is in contact with the biological liquid. Aspiration of the contents of the tube is created by activating the piston 5 by drawing on the base 6. This piston 5 has a course defined by the pin that slides in the groove 14 enabling aspiration of the liquid. Several back and forth movements of the piston (top to bottom movements) enable filling of the chamber 4 and in the case of the presence of a first solution of reagents, mixing of the blood with the first reagent solution. Piston 5 is immobilized in the open position by means of pin 19 retained in the lower part of the groove 14. Then the device is placed on its base 6 for a period of 20 min to 60 h. Advantageously, the device is placed in a thermoregulated chamber between 30° C. and 37° C. in order to facilitate the growth of the microorganisms. During this incubation period the red blood cells sediment in the lower volume 10. The pellet is particularly compact and irreversible given that the blood has been mixed and is incubated with the first reagent solution containing agglutinins.

The separation zone 7 consists of a bottleneck 18 the form of which facilitates sedimentation before the passage into the lower volume 10. The lower volume 10 extends under the bottleneck 18 and the closure means 8 is constructed to close said bottleneck 18 when the piston 5 is in the closing position in order to isolate the lower volume 10 from the upper volume 11. For example, the bottleneck 18 has an approximately conical annular shape extending into the upper volume 4. This shape guarantees maximum agglutination before the passage into the lower volume 10.

The use of agglutinins makes it possible to obtain a dense pellet with exclusion of liquids and less loss of bacteria within the network of sedimented red blood cells. After incubation, the piston 5 is released from its open position by rotation of the base 6 and is carefully pushed so that pin 19 slides into groove 14 up to its closing position. Piston 5 is immobilized in the closing position by means of the pin 19 retained in the extreme part of the groove 14. Piston 5 carries along the closure means 8, which hermetically closes the bottleneck 18, isolating the pellet of red blood cells in the lower volume 10. The upper volume 9 contains the plasma part, the blood platelets, the white blood cells and the bacteria. The longer the incubation time, the higher the concentration of bacteria. The following step is characterized by the introduction of a second reagent solution with platelet aggregation properties. The body of the pump that was positioned in the first step on the receiving element 16 is manually unscrewed, owing to the windows 17 enabling direct access to the pump body, and removed. A syringe with a Luer tip and containing a second reagent solution is positioned and screwed in its place. The solution is introduced into the upper volume 9. Shaking by turning over the device is applied enabling the solution to be mixed with the supernatant derived from the previous step. Device 1 is then placed on a tipping shaker horizontally to the perpendicular of the shaker axis for 30 min to 6 h. Advantageously, the shaker carrying the device is placed in a thermoregulated chamber between 30° C. and 37° C. in order to facilitate the growth of the microorganisms. During this incubation period, the platelets aggregate in the upper volume 9. The longer the incubation time, the higher the concentration of bacteria. The following step may be carried out in different ways:

According to a first embodiment, at the end of incubation the device is turned over, piston 5 towards the top and the skirt towards the bottom, syringe still in position, and a stopper 21 for intake of air 20 is slightly unscrewed and the contents of the upper volume 9 are aspirated into the syringe, the device is put back in the upright position, piston 5 towards the bottom and the skirt towards the top, and the syringe is then unscrewed, a first 5-.mu.m upper porosity filter is positioned by a Luer connector on said syringe itself connected in line to a membrane support containing a membrane, second filter with porosity of 0.2-1 .mu.m, the contents of the syringe sequentially pass through the first filter that retains the microorganisms. The support of the second filter is open and the membrane is recovered for analysis of the microorganisms retained. An example of filter support is given in the patent US-2004/0208796.

According to a second embodiment, at the end of incubation, the syringe positioned in the previous step is unscrewed and a first and second in-line filter are inserted in its place at the level of the Luer connector 15 protected by the skirt, a first filter with porosity greater than 5 .mu.m placed directly in contact with the skirt and a second filter with porosity of 0.2-1 .mu.m inserted in a support (example US-2004/0208796) and located in line with the first filter, the device is turned over, piston 5 towards the top and skirt towards the bottom, and the filter support is connected to a vacuum source, the stopper 21 for intake of air 20 is slightly unscrewed, the vacuum is applied, the contents of the upper volume 9 pass sequentially through the first filter that retains the platelet aggregates and the white blood cells and through the second filter that retains the microorganisms. The device and the first filter are detached from the filter support, the support of the second filter is opened, and membrane is recovered for analysis of the microorganisms retained.

Advantageously, it is possible to sample 1 mL of filtrate at the end of the filtration step; to do that the device is turned over, piston 5 towards the top and skirt towards the bottom, syringe still in place, the stopper 21 for intake of air 20 is slightly unscrewed and part of the volume contained in the upper volume 9 is aspirated into the syringe, the device is put back in upright position, piston 5 towards the bottom and skirt towards the top and the syringe is then unscrewed and the analysis step can take place. This volume of filtrate contains the possible integrated microorganisms and could be used as a sample intended for an antibiogram.

The value of the method and the device described in the present invention is to isolate and concentrate the microorganisms of a blood sample in several hours. Two protocols are proposed, in the first, the first incubation lasts 20 min and the second incubation lasts 4 h at 35-37° C., and in the second protocol called "night protocol" the first incubation lasts more than 12 h at 35-37° C. and the second incubation lasts 30 min. The microorganisms are isolated and concentrated on a filtration membrane in a minimum time of 4 h 20 min from a sample of 1-15 mL of whole blood. This membrane may then be treated for molecular biology analysis, for example.

The proposed examples are carried out with solutions of reagents:

First solution: 9 mL in chamber 4, it is composed of reagents accelerating the sedimentation of the red blood cells and the growth of bacteria:
TSB, Brain-Heart (25%, 75%);
PEG 35 000 1% (w/v);
Lectin 6.66 µg/mL;
Osmosed water.

Second solution: 1.2 mL added into chamber 4, it is composed of reagents enabling the aggregation of platelets and the growth of bacteria:
TSB, Brain-Heart (25%, 75%);
CD9 45 mg/L.

EXAMPLE 1

Removal of the Red Blood Cells and the Platelets 3-5 mL of whole blood are sampled in the device 1 containing 9 mL of the first reagent solution as described previously. The device is placed for 30 min on its base 6 in vertical position at room temperature. The pellet of red blood cells (RBC) formed is isolated by action at the piston 5. The supernatant (SN) is recovered. A count of the red blood cells and platelets in the supernatant (RBC in SN and PLT in SN) is carried out with a cell counter (Micros 60, ABX, France). For one of the samples, the method is continued by the addition of the second reagent solution, incubation under overnight shaking (approximately 16 h) then upper 5-μm filtration of the entire supernatant. A count of the platelets (PLT) is carried out with a cell counter (Micros 60, ABX, France).

The results are summarized in Table 1. The number of RBC in the sample (RBC in sample) is calculated starting from a theoretical concentration of RBC of $4 \times 10^6/\mu L$. Likewise, the number of PLT (PLT in the sample) is calculated starting from a theoretical value of $300 \times 10^3/\mu L$. After sedimentation and isolation of the RBC, the number of residual red blood cells in the supernatant is divided by 50-100 and the number of residual platelets by 5. After platelet aggregation and filtration, this number is divided by 10.

In this example, the method and the device enable a reduction of approximately 2 Log of red blood cells and approximately 1 Log of platelets.

EXAMPLE 2

Recovery of the Microorganisms

A sample of whole blood is contaminated experimentally with 4 bacterial strains: *Staphylococcus epidermidis* (SE), *Staphylococcus aureus* (SA), *Escherichia coli* (EC) and *Pseudomonas aeruginosa* (PA) at approximately 100 bacteria/mL. A volume of blood is introduced into the device 1 and incubated in chamber 4 with 9 mL of the first reagent solution. The device is placed for 30 min on its base 6 in the vertical position at room temperature. The pellet of red blood cells formed is isolated by action of the piston 5. The supernatant (SN) is recovered. The method is continued by the addition of the second reagent solution and incubation under shaking for 4 h in a thermoregulated chamber at 35-37° C. A count of bacteria on a Petri dish is carried out at the start of the incubation at 35-37° C. at T0 and after 2 h of incubation, at T2H and after 4 h of incubation, at T4H. The colonies on the Petri dishes are counted 24-48 h after deposit.

The results are presented in Table 2. The 4H incubation allows significant growth of the bacteria, the number of which is multiplied by 25 for SE which is known as a slow-growing bacterium, up to 9,000 for EC which is known as a rapid-growing bacterium. These concentrations are compatible with a molecular biology detection method.

Results expressed in number of colonies/mL of supernatant

The invention claimed is:

1. A device for preparation of a fluid sample for analysis, comprising:
   a container comprising an upper part and a lower part that configured to be connected to each other to together form a chamber, said lower part comprising a base, wherein the upper part comprises a stopper configured to allow air intake into the upper volume, when unscrewed;
   a piston that extends from the base of the lower part into the chamber, said piston comprising a closure means, said piston being movable between an open position and closed position, wherein when the piston is in a closed position, the closure means of the piston separates the chamber into an upper volume and a lower volume, and wherein when the piston is in an open position, the upper volume and lower volume are in fluid communication;
   a separation zone that defines a bottleneck, wherein the lower volume extends under the bottleneck, wherein the closure means cooperates with the separation zone in order to define the upper volume and lower volume; and
   a means for introduction of a the fluid into the upper volume of the chamber.

2. The device of claim 1, wherein the bottleneck has an approximately conical annular shape extending into the upper volume.

3. The device of claim 1, wherein the piston comprises a rod with one end extending from the base of the lower part into the lower volume of the chamber, said lower volume extending around said rod, wherein the end of the rod extending into the lower volume comprises a protuberance that forms the closure means by sealing the bottleneck when the piston is in a closed position.

4. The device of claim 1, wherein the container comprises a guiding groove having a first extreme part and a second extreme part, wherein the piston comprises a pin arranged in said groove, wherein when the pin is arranged at the first extreme part of the groove, the piston is in the open position, and wherein when the pin is arranged in the second extreme part of the groove, the piston is in the closed position.

5. The device of claim 1, wherein the chamber contains a first reagent solution for accelerating the sedimentation of the fluid and growth of microorganisms, if present, in the fluid sample.

TABLE 1

| Volume of Blood Sample (mL) | RBC in Sample | PLT in Sample | SN (mL) | RBC in SN | PLT in SN | PLT in Filtrate |
|---|---|---|---|---|---|---|
| 4 | $16 \times 10^9$ | $12 \times 10^8$ | 7 | $2.8 \times 10^8$ | $4.3 \times 10^8$ | |
| 4 | $16 \times 10^9$ | $12 \times 10^8$ | 7 | $2.8 \times 10^8$ | $5.6 \times 10^8$ | |
| 5 | $2 \times 10^{10}$ | $15 \times 10^8$ | >7 | $2 \times 10^8$ | $7.4 \times 10^8$ | |
| 4.5 | $18 \times 10^9$ | $14 \times 10^8$ | >7 | $2 \times 10^8$ | $6.2 \times 10^8$ | |
| 3 | $12 \times 10^9$ | $9 \times 10^8$ | 7 | $2 \times 10^8$ | $1.2 \times 10^8$ | |
| 3.5 | $14 \times 10^9$ | $11 \times 10^8$ | 7 | $2 \times 10^8$ | $3.5 \times 10^8$ | $10^8$ |
| 4 | $16 \times 10^9$ | $12 \times 10^8$ | 7 | $2 \times 10^8$ | $3.3 \times 10^8$ | |

TABLE 2

| | SE | SA | EC | PA |
|---|---|---|---|---|
| T0 | 40 | 60 | 130 | 450 |
| T2H | 220 | 350 | 1450 | 1020 |
| T4H | 1000 | 6000 | 1190000 | 49000 |

6. The device of claim 1, wherein the means for introduction of the fluid comprises a Luer connector located above the chamber, said Luer connector being configured to receive a second container for housing the fluid to be introduced into the chamber.

7. The device of claim 6, wherein the upper part comprises a window that enables access to the Luer connector.

8. The device of claim 6, wherein the upper part of the container comprises a receiving part, said receiving part comprising a skirt that receives the second container for housing the fluid to be introduced into the chamber, and the Luer connector.

9. The device of claim 8, wherein the second container for housing the fluid to be introduced into the chamber comprises a pump body with a needle.

10. The device of claim 8, further comprising a syringe with a Luer tip is positioned on the receiving part.

11. The device of claim 8, further comprising a filter support with a Luer tip is positioned on the receiving part.

12. The device of claim 11, wherein the filter support comprises a first and a second in-line filter.

13. The device of claim 12, wherein the first in-line filter has a porosity grater than 5 μm.

14. The device of claim 12, wherein the second in-line filter has a porosity between 0.2-1 μm.

15. A method for preparation of a fluid sample for analysis, said method comprising:
   providing the device of claim 1;
   introducing the fluid sample into the chamber, when piston is in the open position;
   allowing the sedimentation of the sample fluid, such that a pellet and a supernatant are generated;
   moving the piston to its closed position following said sedimentation step, thereby separating the sediment pellet from the supernatant, wherein the pellet is localized in the lower volume and the supernatant is localized in the upper volume;
   mixing the supernatant with a solution of reagents to promote the growth of microorganisms, if present, in the supernatant.

16. The method according to claim 15, wherein the is the introducing step further comprises mixing the fluid sample with a first reagent solution that accelerates the sedimentation of the fluid sample and the growth of microorganisms, if present, in the fluid sample.

17. The method of claim 15, further comprising incubating and filtering the supernatant after the mixing step.

18. The method of claim 15, wherein the fluid sample introduced into the chamber has a volume between 1 mL and 15 mL.

19. The method of claim 15, wherein the fluid sample is whole blood, and the sediment pellet comprises red blood cells.

* * * * *

UNITED STATES PATENT AND TRADEMARK OFFICE
CERTIFICATE OF CORRECTION

PATENT NO.       : 8,709,796 B2                                             Page 1 of 1
APPLICATION NO. : 11/995355
DATED            : April 29, 2014
INVENTOR(S)      : Faure et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1804 days.

Signed and Sealed this

Twenty-ninth Day of September, 2015

Michelle K. Lee
*Director of the United States Patent and Trademark Office*